(12) United States Patent
Shirley (10) Patent No.: US 7,854,759 B2
(45) Date of Patent: Dec. 21, 2010

(54) PROSTHETIC FLOW MODIFYING DEVICE

(75) Inventor: Gary B. Shirley, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 61 days.

(21) Appl. No.: 12/337,124

(22) Filed: Dec. 17, 2008

(65) Prior Publication Data

US 2009/0164000 A1 Jun. 25, 2009

Related U.S. Application Data

(60) Provisional application No. 61/016,208, filed on Dec. 21, 2007.

(51) Int. Cl.
*A61F 2/06* (2006.01)
(52) U.S. Cl. ............... 623/1.24; 623/2.14; 606/200
(58) Field of Classification Search .............. 623/1.24, 623/2.14; 600/200
See application file for complete search history.

(56) References Cited

U.S. PATENT DOCUMENTS

| | | | |
|---|---|---|---|
| 7,442,204 B2 * | 10/2008 | Schwammenthal et al. | 623/1.24 |
| 7,442,206 B2 * | 10/2008 | Flagle et al. | 623/2.1 |
| 7,618,447 B2 * | 11/2009 | Case et al. | 623/1.26 |
| 7,670,368 B2 * | 3/2010 | Hill et al. | 623/1.24 |
| 7,686,844 B2 * | 3/2010 | Case et al. | 623/1.24 |
| 2008/0091261 A1 * | 4/2008 | Long et al. | 623/1.24 |
| 2008/0103586 A1 * | 5/2008 | Styrc et al. | 623/1.24 |
| 2009/0105810 A1 * | 4/2009 | Jaffe | 623/1.24 |

* cited by examiner

*Primary Examiner*—Suzette J Gherbi
(74) *Attorney, Agent, or Firm*—Buchanan Nipper (57) ABSTRACT

An implantable flow modifying device and a method of modifying flow through a lumen are provided. The flow modifying device includes a flexible member configured for permitting fluid flow through the body lumen in a first direction at a first rate and for restricting fluid flow through the body lumen in a second direction at a second rate. The flexible member includes a passageway defined by a sheath of biocompatible material, the passageway having a first end portion and a second end portion. The first end portion is sized and shaped to at least partially restrict fluid flow in the first direction and capable of at least partially collapsing in response to fluid flow in the second direction. The second end portion is adapted to seal with a wall of the body lumen. A diameter of a first opening defined in the first end portion is smaller than a diameter of a second opening defined in the second end portion.

14 Claims, 7 Drawing Sheets

PROSTHETIC FLOW MODIFYING DEVICE

RELATED APPLICATIONS

This application claims the benefit under 35 U.S.C. §119(e) of U.S. Provisional Application Ser. No. 61/016,208, filed Dec. 21, 2007, which is incorporated herein by reference in its entirety.

FIELD OF THE INVENTION

The present invention relates to medical devices, and in particular to prosthetic flow modifying devices, methods of making such devices, and methods of deploying such devices within a body site.

BACKGROUND

Many vessels in animals transport fluids from one bodily location to another. Frequently, fluid flows in a substantially unidirectional manner along the length of the vessel. For example, veins in the body transport blood to the heart and arteries carry blood away from the heart.

In mammalian veins, natural valves are positioned along the length of the vessel in the form of leaflets disposed annularly along the inside wall of the vein which open to permit blood flow toward the heart and close to restrict back flow. These natural venous valves open to permit the flow of fluid in the desired direction, and close upon a change in pressure. When blood flows through the vein, the pressure forces the valve leaflets apart as they flex in the direction of blood flow and move towards the inside wall of the vessel, creating an opening therebetween for blood flow. When the pressure differential across the valve, the flow velocity, or both change, the leaflets return to a closed position to restrict or prevent blood flow in the opposite, i.e. retrograde, direction. The leaflet structures, when functioning properly, extend radially inwardly toward one another such that the tips contact each other to restrict backflow of blood.

In the condition of venous insufficiency, the valve leaflets do not function properly. Incompetent venous valves can result in symptoms such as swelling and varicose veins, causing great discomfort and pain to the patient. If left untreated, venous insufficiency can result in excessive retrograde blood flow through incompetent venous valves, which can cause venous stasis ulcers of the skin.

There generally are two types of venous insufficiency: primary and secondary. Primary venous insufficiency typically occurs where the valve structure remains intact, but the vein is simply too large in relation to the leaflets so that the leaflets cannot come into adequate contact to prevent backflow. More common is secondary venous insufficiency, where the valve structure is damaged, for example, by clots which gel and scar, thereby changing the configuration of the leaflets, i.e. thickening the leaflets and creating a "stub-like" configuration. Venous insufficiency can occur in the superficial venous system, such as the saphenous veins in the leg, or in the deep venous system, such as the femoral and popliteal veins extending along the back of the knee to the groin.

A common method of treatment of venous insufficiency is placement of an elastic stocking around the patient's leg to apply external pressure to the vein. Although sometimes successful, the tight stocking is quite uncomfortable, especially in warm weather, as the stocking must be constantly worn to keep the leaflets in apposition. The elastic stocking also affects the patient's physical appearance, thereby potentially having an adverse psychological affect. This physical and/or psychological discomfort can lead to the patient removing the stocking, thereby preventing adequate treatment.

Surgical methods for treatment of venous insufficiency have also been developed. A vein with incompetent venous valves can be surgically constricted to bring incompetent leaflets into closer proximity in an attempt to restore natural valve function. Methods for surgical constriction of an incompetent vein include implanting a frame around the outside of the vessel, placing a constricting suture around the vessel, or other types of treatment of the outside of the vessel to induce vessel contraction. Other surgical venous insufficiency treatment methods include bypassing or replacing damaged venous valves with autologous sections of veins with competent valves. However, these surgeries often result in a long patient recovery time and scarring, and carry the risks, e.g. anesthesia, inherent with surgery.

Recently, various implantable prosthetic devices and minimally invasive methods for implantation of these devices have been developed to treat venous insufficiency, without the disadvantages of treatment with an outer stocking or extensive surgery. Such prosthetic venous valve devices can be inserted intravascularly, for example from an implantation catheter. Prosthetic devices can function as a replacement valve, or restore native valve function by bringing incompetent valve leaflets into closer proximity or by modifying the flow through the vessel.

Valves for implantation into veins are known in the art having leaflets positional to allow fluid flow through a vessel in a first direction and to restrict fluid flow through the vessel in a second direction. Examples of such prosthetic valves are described in commonly owned U.S. Pat. No. 7,153,324 and U.S. Publication No. 2004/0260389.

It is desirable to have prosthetic devices for modifying fluid flow through a vessel that permit fluid flow in a first direction and wherein the devices are at least partially collapsible in a second direction to modify fluid flow therethrough.

BRIEF SUMMARY

In one aspect of the present invention, an implantable prosthetic device for modifying fluid flow through a body lumen is provided. The flow modifying device includes a flexible member configured for permitting fluid flow through the body lumen in a first direction at a first rate and for restricting fluid flow through the body lumen in a second direction at a second rate. The flexible member includes a passageway defined by a sheath of biocompatible material, the passageway having a first end portion and a second end portion. The first end portion is sized and shaped to at least partially restrict fluid flow in the first direction and capable of at least partially collapsing in response to fluid flow in the second direction. The second end portion is adapted to seal with a wall of the body lumen. A diameter of a first opening defined in the first end portion is smaller than a diameter of a second opening defined in the second end portion.

In another aspect of the present invention, a prosthetic flow modifying device for implantation into a body vessel is provided. The flow modifying device includes a flexible member moveable between an open configuration and a closed configuration. The flexible member includes a passageway defined by a sheath of biocompatible material where the passageway has a first end portion and a second end portion operably connected to the first end portion. A frame is operably connected to the second end portion. The first end portion at least partially restricts fluid flow through the passageway in the open configuration and the first end portion is at least partially collapsible toward the second end portion to form the closed configuration when fluid flow is in a second direction.

In another aspect of the present invention, a method of modifying flow through a lumen is provided. The method includes providing a passageway defined by a sheath of biocompatible material, the passageway having a first end portion and a second end portion. The first end portion is sized and shaped to at least partially restrict fluid flow in the first direction and capable of at least partially collapsing in response to fluid flow in the second direction. The method further includes delivering the flexible member to the lumen using a delivery device and attaching the flexible member to the lumen so that the second end portion forms a seal with the lumen and the first end portion is unattached and movable in response to fluid flow through the passageway.

Advantages of the present invention will become more apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

DETAILED DESCRIPTION OF THE INVENTION

As described herein, a prosthetic flow modifying device for implantation into a body vessel is provided. The term "vessel" as used herein includes ducts, canals, and other passageways in the body, as well as cavities and other locations. For example, the flow modifying devices of the present invention are suitable for implantation into the vessels of the vasculature, such as veins, for regulating fluid flow through the vessel. The flow modifying devices of the present invention may also be implanted in a passageway of the heart to regulate the fluid flow into and out of the heart. As used herein, the term "implantable" refers to an ability of a medical device to be positioned at a location within a body, such as within a body vessel, either temporarily, semi-permanently, or permanently. Permanent fixation of the device in a particular position is not required. Furthermore, the terms "implantation" and "implanted" refer to the positioning of a medical device at a location within a body, such as within a body vessel.

Figure 1A:
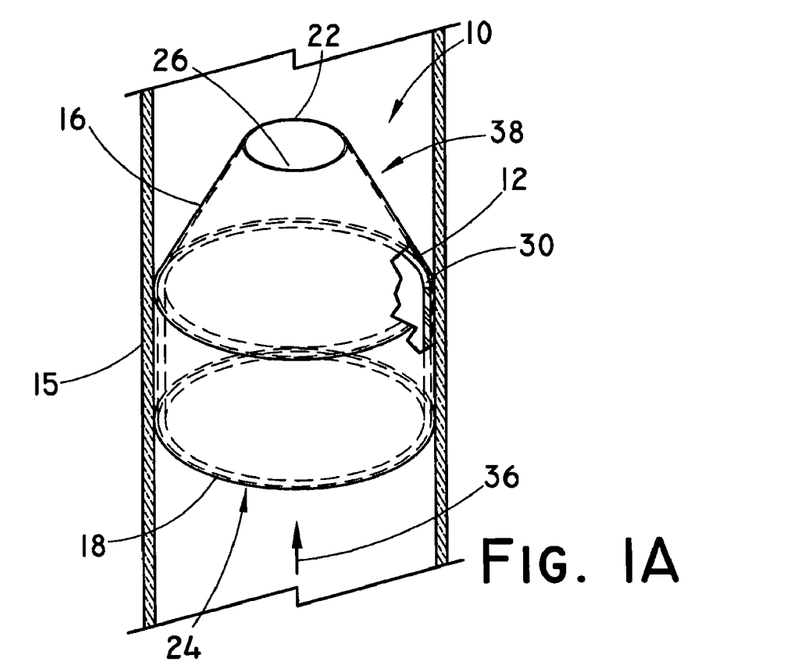
FIG. 1A is a side view of an embodiment of the prosthetic flow modifying device of the present invention showing an open configuration.
Figure 1B:
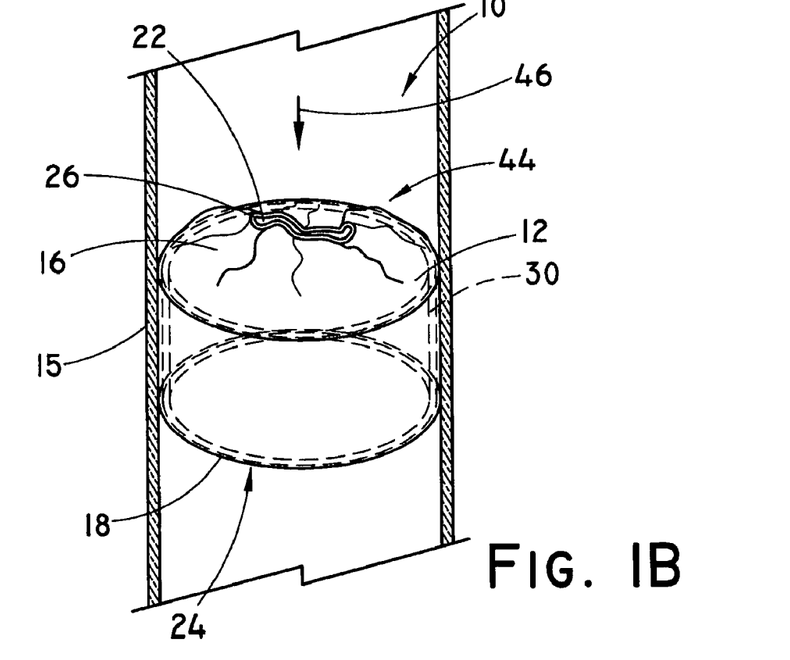
FIG. 1B is a side view of an embodiment showing a closed configuration.

An embodiment of the prosthetic flow modifying device 10 of the present invention is shown in FIGS. 1A and 1B and described with respect to implantation into a vessel wall 15. The flow modifying device 10 includes a flexible member 12 having a first end portion 16 and a second end portion 18. The first end portion 16 includes a first opening 22 and the second end portion 18 includes a second opening 24. A lumen 26 is defined through the flexible member 12 between the openings 22 and 24. The flexible member 12 may be connected to a frame 30. The flexible member 12 is movable in response to fluid flow through the device 10 and the opening 22 may be reshaped in response to the movement of the flexible member 12.

The flexible member 12 may be formed from flexible materials (described in detail below) that can conform to the shape of the vessel wall 15 as the shape of the vessel changes in response to pressure changes within the body. In some embodiments, the flow modifying device 10 includes at least a portion, for example, the second end portion 18, that is sized and shaped to fit against the vessel wall 15 and substantially prevents fluid flow around the flow modifying device 10 rather than through the lumen 26. As shown in FIGS. 1A and 1B, the second end portion 18 is operably connected to the vessel wall 15 and the first end portion 16 is unconnected to the vessel wall 15 and freely movable. The freely movable first end portion 16 may help to keep blood from stagnating or forming a thrombus at the device 10.

The flexible member 12 is movable in response to fluid flow in a first direction 36, i.e. towards the heart, where the flow modifying device 10 is in an open configuration 38 as shown in FIG. 1A. In the open configuration 38, the opening 22 of the flexible member may be in a fully open configuration for fluid flow therethrough at a first rate. As shown in FIG. 1A, the first opening 22 is smaller than the second opening 24 reducing the flow rate through the lumen 26 in comparison to a vessel without the prosthetic device 10 implanted therein. As shown in FIG. 1B, the device 10 is in a closed configuration 44 when the fluid flow is in a second direction 46. The first end portion 16 of the flexible member collapses toward the second end portion 24 and reduces the size of the opening 22 thereby reducing the flow though the lumen 26 to a second, slower rate that includes substantially preventing fluid flow through the lumen 26 as well as reducing the rate of flow therethrough.

Figure 2A:
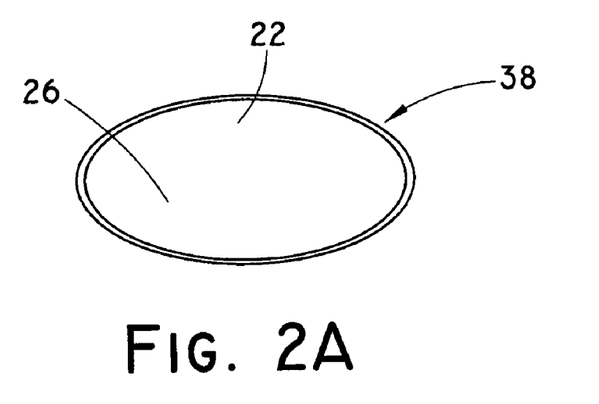
FIG. 2A is a partial top view of the embodiment shown in FIG. 1A in an open configuration.
Figure 2B:
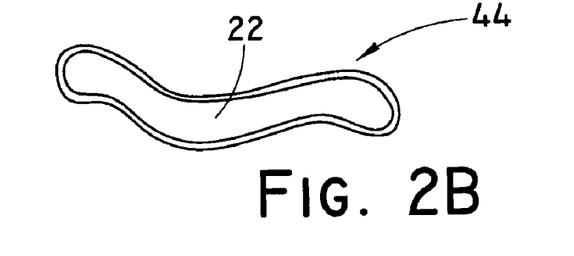
FIG. 2B is a partial top view of the embodiment shown in FIG. 1B in a closed configuration.
Figure 2C:
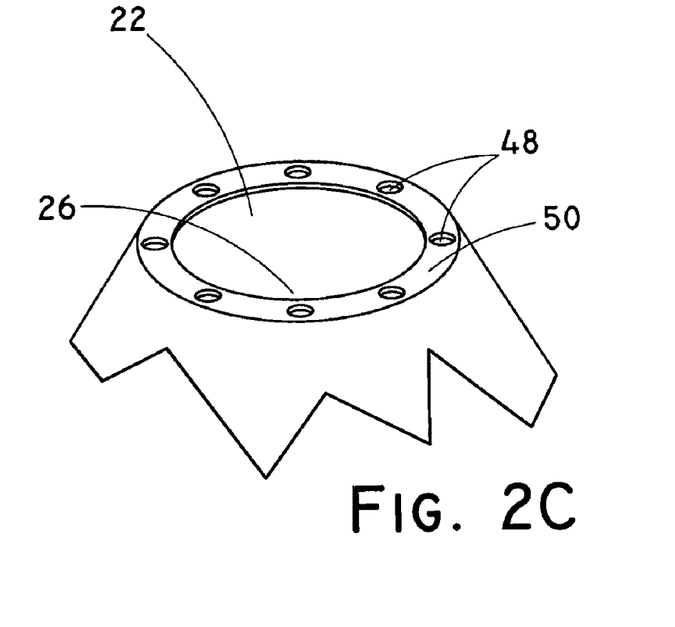
FIG. 2C is an alternative embodiment of the top view shown in FIG. 2A in the open configuration.

Top views of the open configuration 38 and the closed configuration 44 are shown in FIGS. 2A and 2B, respectively. As shown, the opening 22 of the lumen 26 decreases in size, decreasing the amount of fluid flow therethrough, between the open configuration 38 that results from fluid flow in the first direction 36 and the closed configuration 44 when fluid flows in the second direction 46. in some embodiments, the fluid flow through the lumen 26 may be decreased by an edge portion at the opening. See, for example, edge 50 shown in FIG. 2C and edge 250 shown in FIG. 5. As will be understood by one skilled in the art, some retrograde flow through the opening 22 of the device 10 may occur when fluid flow is in the second direction 46. By way of non-limiting example, in some embodiments, the flow modifying device 10 may include one or more openings 48 in an edge portion 50 of the opening 22 as shown in FIG. 2C. Openings 48 may also be provided in the flexible member 12 between the openings 22, 24 (not shown). The openings 48 may allow some retrograde flow through the flow modifying device 10 when fluid flow is in the second direction 46 and the first end portion 16 is collapsed toward the second end portion 18 as shown in FIG. 1B. In some embodiments, the opening 22 may be completely closed when the flow modifying device 10 is in the closed configuration 44 such that no retrograde flow occurs through the opening 22 although retrograde flow may still occur through openings 48, if present.

Figure 6A:
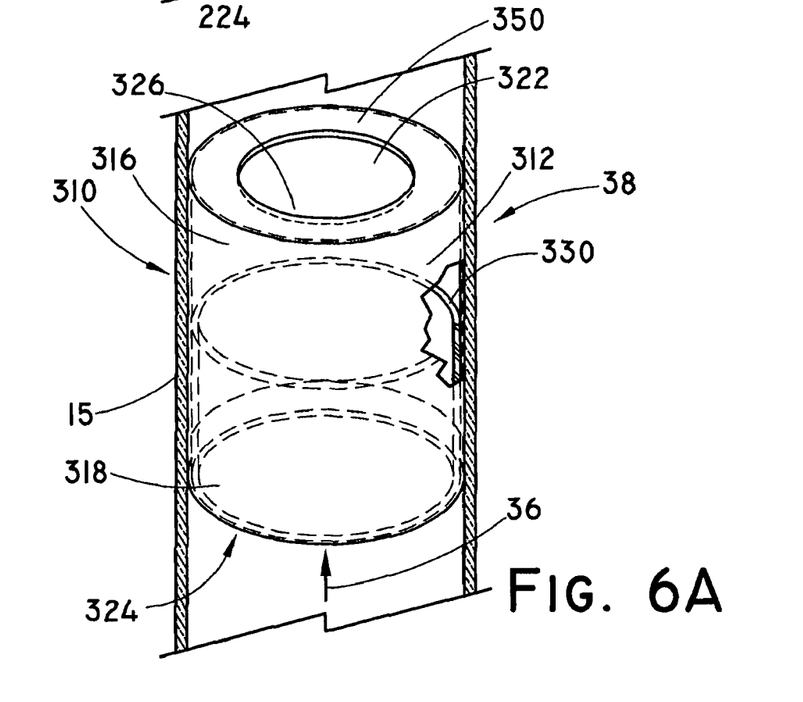
FIG. 6A is a side view of an alternative embodiment shown in the open configuration.

The flow modifying device 10 may have any size and shape suitable for implantation into a bodily vessel. As shown in FIG. 1A, the device 10 may be conically shaped wherein the flexible member 12 may be widest at the second end portion 18 and tapers inward at the first end portion 16 when the flow modifying device is in the open configuration 38. In some embodiments, the device 10 may be tubular in shape wherein the first end portion 16 is about the same width as the second end portion 18 in the open configuration 38 as shown in FIG. 6A. The first end portion 16 may also be rounded, ovoid, arched and the like.

Figure 3:
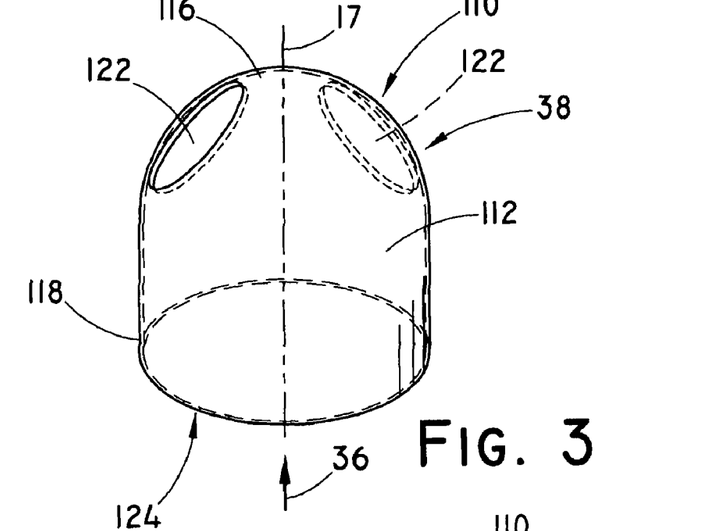
FIG. 3 is a side view of an alternative embodiment shown in the open configuration and having at least two openings.
Figure 4A:
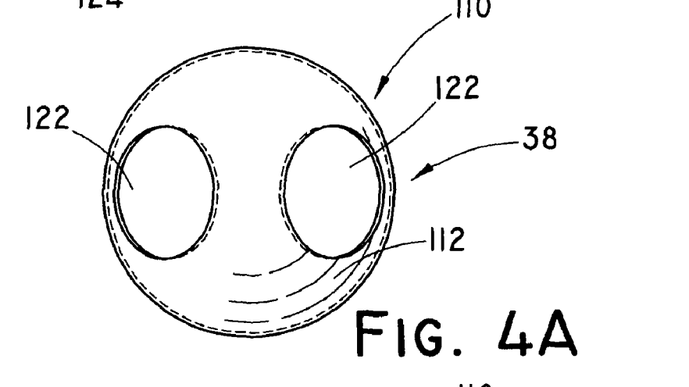
FIG. 4A is a partial top view of the embodiment shown in FIG. 3 in an open configuration.
Figure 4B:
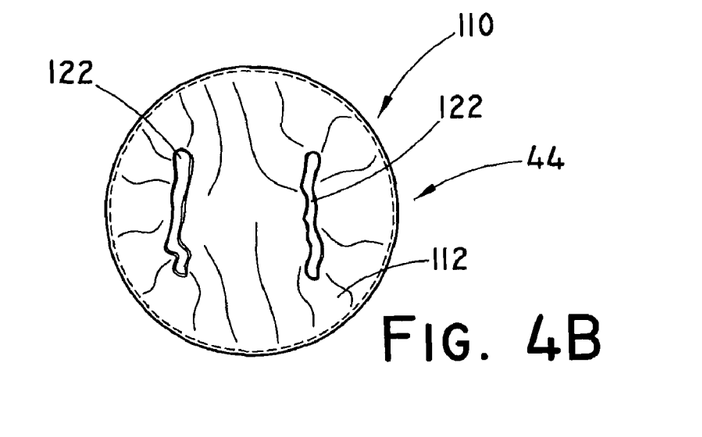
FIG. 4B is a partial top view of the embodiment shown in FIG. 3 in a closed configuration.

The device 10 may include one or more openings 22 in the first end portion 16. In some embodiments, the opening 22 may be centrally located, for example, as shown in FIG. 1A. Alternatively, as shown in FIG. 3, a flow modifying device 110 may include one or more openings 122 that are off-set from a central axis 17 through the vessel 15. The device 110 includes a flexible member 112 having a first end portion 116 and a second end portion 118 similar to the flow modifying device 10 described above. The flexible member 112 extends between the openings 122 at the first end portion 116. The device 110 also includes an opening 124 in the second end portion 118. The device 110 is shown in the open configuration 38 in response to fluid flow in the first direction 36. FIG. 4A illustrates the top view of the device 110 in the open configuration 38 with the openings 122 opened to allow fluid flow therethrough. FIG. 4B illustrates the flow modifying device 110 in the closed configuration 44 wherein the first end portion 116 has collapsed toward the second end portion 118 and the openings 122 are collapsed together to reduce or eliminate fluid flow therethrough when the fluid flows in the second direction 46.

As discussed above, some retrograde flow through the openings 122 is possible. Optionally, additional small openings, similar to the openings 48 described above, may be included in the flexible member 112 to allow for retrograde flow through the openings when the flow modifying device 110 is in the closed configuration (not shown). The device 110 may also include one, three, four or more openings 122. The openings 122 may be similarly sized and shaped or the openings 122 may have different sizes and shapes. Similarly, the second end portion 118 may include one, two, three or more openings 124.

Figure 5:
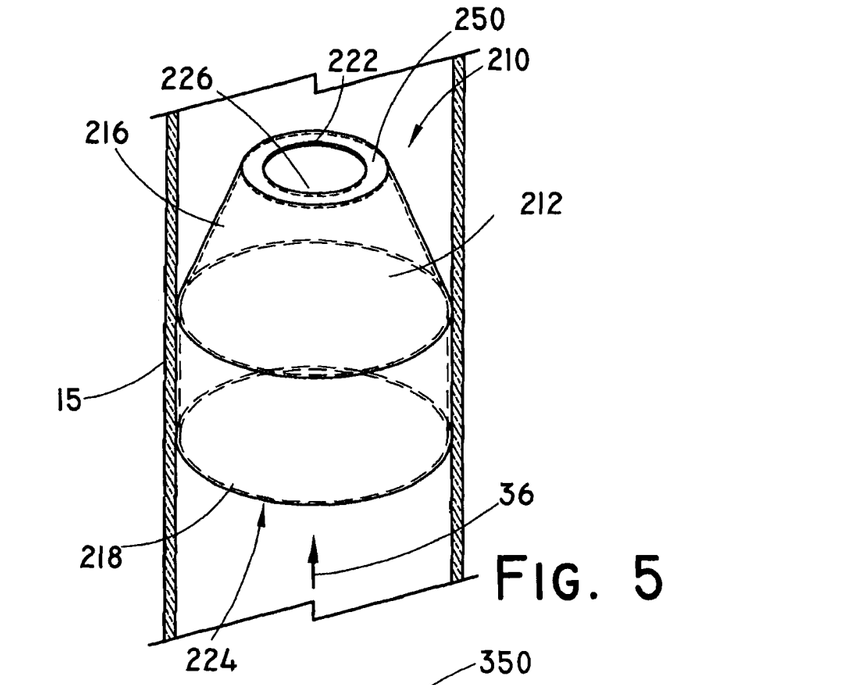
FIG. 5 is a side view of an alternative embodiment shown in the open configuration and having an edge portion.

A flow modifying device 210 is shown in FIG. 5. The device 210 is similar to the previous flow modifying devices described above in that the device 210 includes a flexible member 212, a first end portion 216, a second end portion 218, a first opening 222 and a second opening 224. A lumen 226 is defined between the openings 222 and 224. The first opening 222 may be surrounded by an edge portion 250. The edge portion 250 may be generally perpendicular to the vessel wall 15 into which the device 210 is implanted. The edge portion 250 may reduce flow though the device 210 in the first direction 36 and the second direction 46. The edge portion 250 may be formed from the same material as the flexible member 212 and may be formed as a unitary construction. Alternatively, the edge portion 250 may be separately formed from the same or different materials and connected to the flexible member 212. In some embodiments, the edge portion 250 may be reinforced or stiffened. The edge portion 250 may also be collapsible to substantially close the opening 222 when fluid flow is in the second direction 46, similar to the flow modifying device described above. When the edge portion 250 is reinforced or stiffened, the device 210 may collapse upon itself and a portion of the flexible member 212 may fold inward and overlap with the opening 222 to substantially reduce the flow through the opening 222 in the second direction.

Figure 6B:
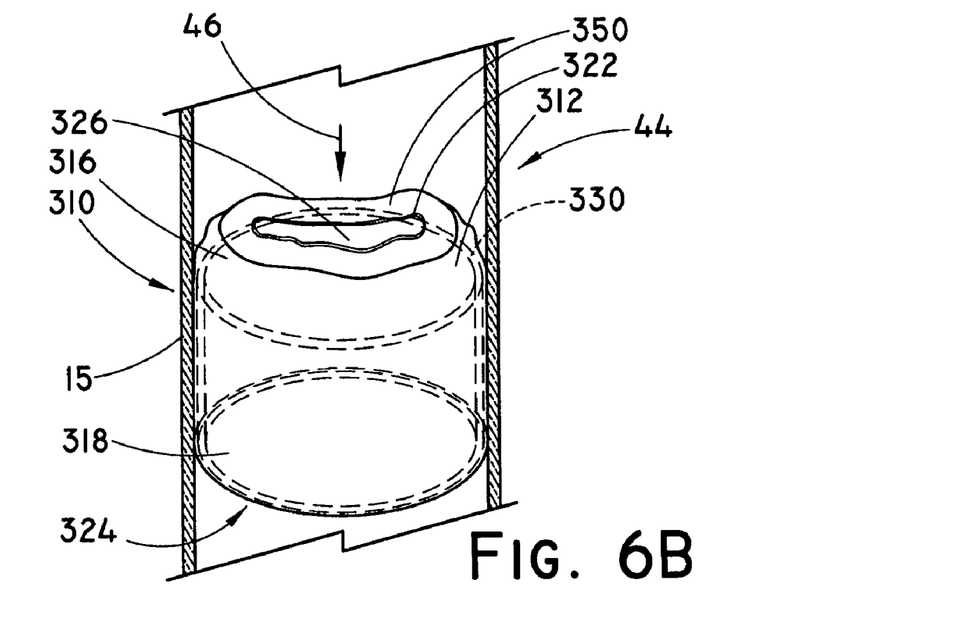
FIG. 6B is a side view of the embodiment shown in FIG. 6A in the closed configuration.
Figure 6C:
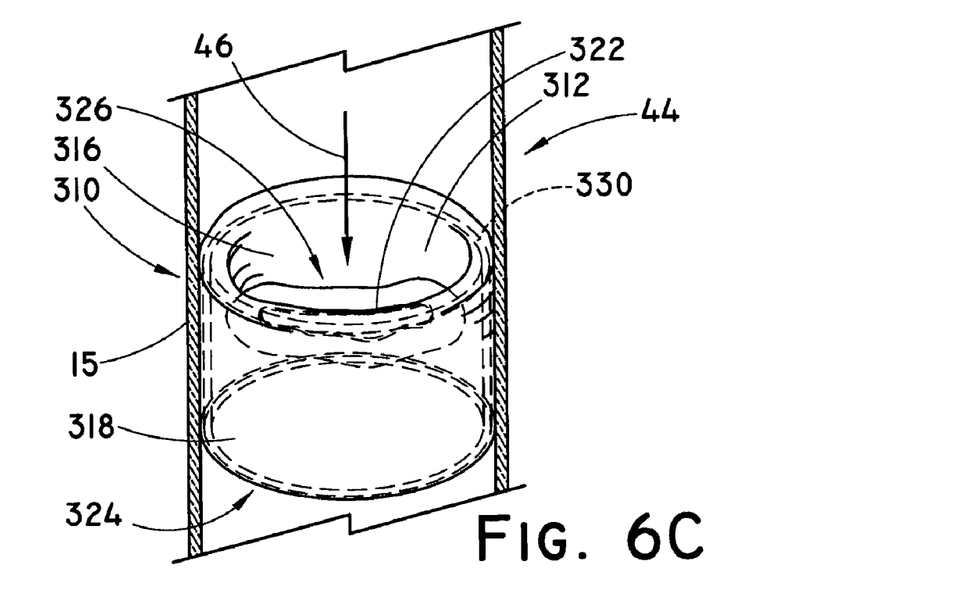
FIG. 6C is a side view of the embodiment shown in FIG. 6a in the closed configuration with the first end portion inverted towards the second end portion.

FIGS. 6A-6C illustrate a flow modifying device 310 having a tubular-shaped flexible member 312. The device 310 is similar to the embodiments described above in that the device 310 includes the flexible member 312, a first end portion 316, a second end portion 318, a first opening 322 and a second opening 324. A lumen 326 is defined between the openings 322 and 324. The first opening 322 may have an edge portion 350 extending inward into the lumen 326 (FIG. 6A) or the first opening 322 may extend straight and be about the same size as the opening 326 (not shown). The device 310 may include a frame 330.

Similar to the embodiment discussed above, the second end portion 318 is operably connected to the vessel wall 15 and the first end portion 316 is unconnected to the vessel wall 15 and freely movable. FIG. 6A illustrates the flow modifying device 310 in the open configuration 38 in response to fluid flow in the first direction 36. The first end portion 316 is fully extended in the direction of fluid flow through the device 310. FIGS. 6B and 6C illustrate the device 310 in the closed configuration 44 in response to fluid flow in the second direction 46. As shown in FIG. 6B, the first end portion may be collapsible on itself to reduce the amount of fluid flow through the opening 322 in the second direction 46. In some embodiments, the first end portion 316 may be collapsible so that the fluid flow through the lumen 326 is substantially prevented when the fluid flow is in the second direction 46. As discussed above, the flow modifying device 310 may include additional small openings, for example in the flexible member 312 to allow some retrograde flow through the device 310 when fluid flow is in the second direction. As shown in FIG. 6C, the flexible member may be configured so that the first end portion 316 is invertible or partially invertible towards the second end portion 318. For example, in response to higher pressure in the second direction 46, i.e., 80 mm Hg, the first end portion 316 may invert toward the second end portion 318. In the embodiments wherein the first end 316 inverts in response to fluid flow in the second direction 46, fluid flow through the lumen 326 may be substantially prevented or reduced, for example, when the first end portion 316 may be partially collapsed inward on itself to reduce the size of the opening 322.

Figure 7A:
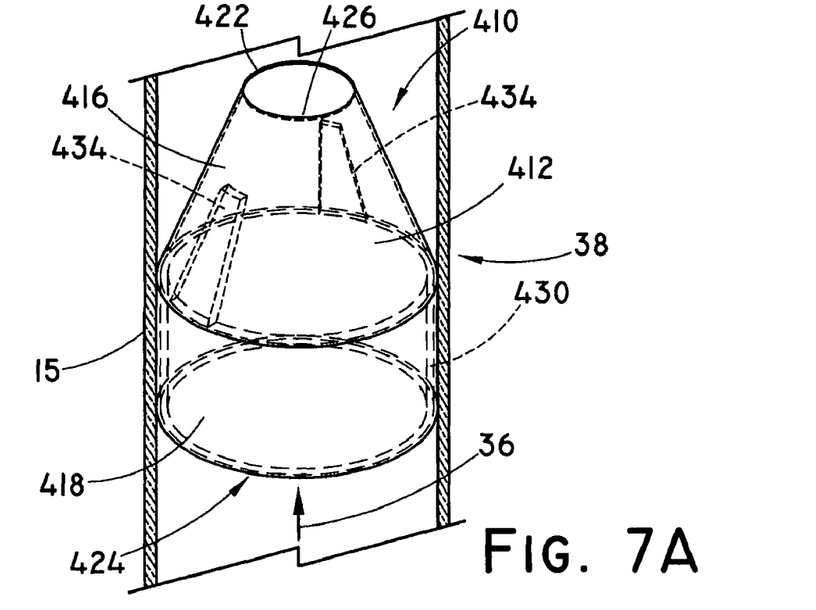
FIG. 7A is a side view of another embodiment of the present invention having a frame with struts extending inwardly with the device in the open configuration.
Figure 7B:
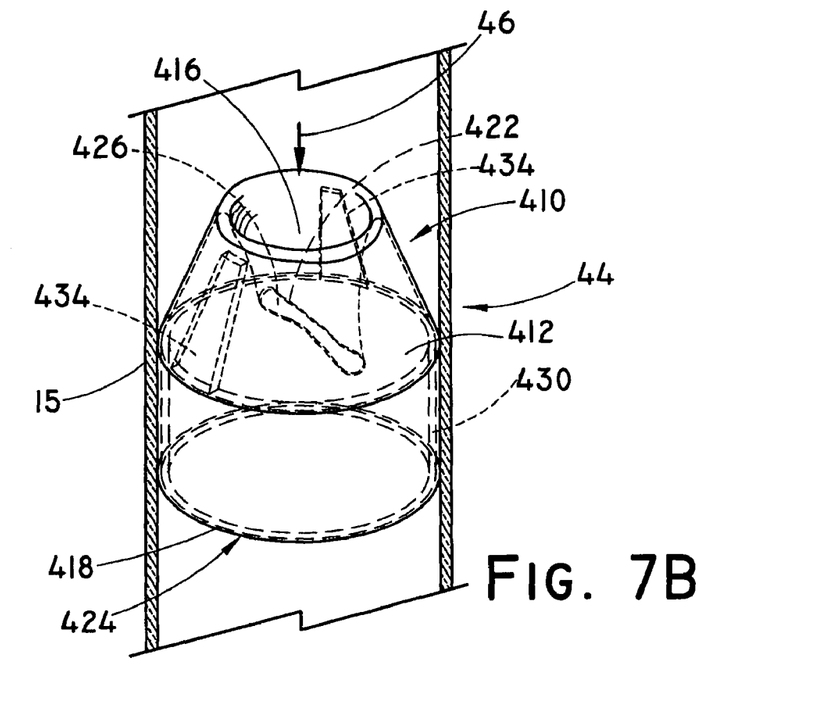
FIG. 7B is a side view of the embodiment shown in FIG. 7A in the closed configuration.

In some embodiments, a flow modifying device 410 may include one or more supports 434 extending inward into a lumen of the vessel wall 15 and operably connected to a portion of a flexible member 412. As shown in FIG. 7A, the device 410 includes the supports 434 extending from a frame 430. A first end portion 416 of the flexible member 412 having an opening 422 defined therein remains free from connection to the frame 430, the supports 434 and the vessel wall 15. A second end portion 418 includes a second opening 424 and a lumen 426 connects the first and second openings 422, 424. The device 410 is shown in the open configuration 38 with fluid flow in the first direction 36 in FIG. 7A. As shown in FIG. 7B, the first end portion may be collapsible on itself to reduce the amount of fluid flow through the opening 422 in the second direction 46. In some embodiments, the first end portion 416 may be collapsible so that the fluid flow through the lumen 426 is substantially prevented when the fluid flow is in the second direction 46. As discussed above, the flow modifying device 410 may include additional small openings, for example in the flexible member 412 to allow some retrograde flow through the device 410 when fluid flow is in the second direction.

Figure 8:
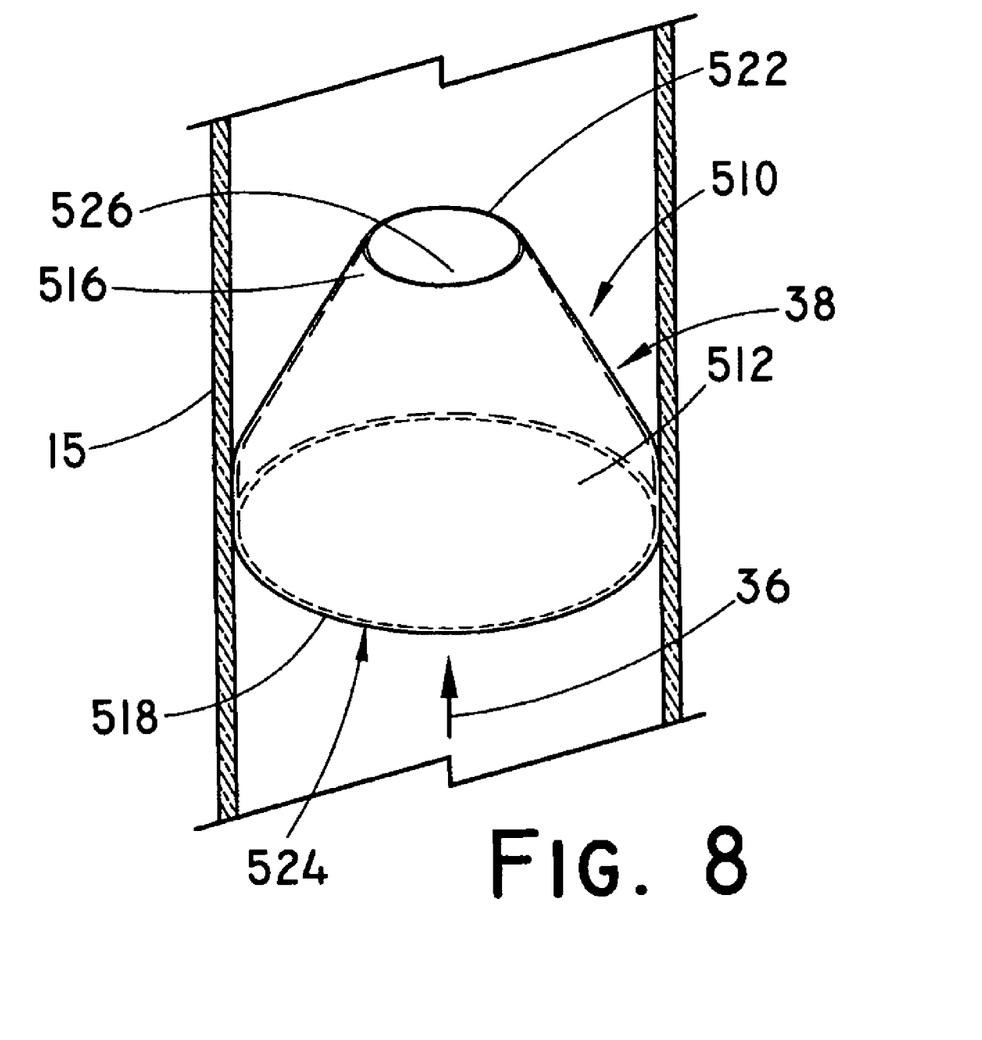
FIG. 8 is a side view of an alternative embodiment of the present invention of a frameless flow modifying device in the open configuration.

In some embodiments, a flow modifying device 510 may be provided without a frame. The flow modifying device 510 includes a flexible member 512 having a first end portion 516, a first opening 522, a second end portion 518 and a second opening 524. A lumen 526 connects the first opening 522 to the second opening 524. The device 510 functions similarly to the embodiments shown above having an open configuration and a closed configuration. As shown in FIG. 8, the device 510 may be attached to the vessel wall 15 at an attachment portion 530 of the second end portion 518. The first end portion 516 is unconnected and freely movable in response to fluid flow through the device 510. FIG. 8 illustrates the flow modifying device 510 in the open configuration 38 with fluid flow in the first direction 36 through the lumen 526. The first end portion 516 of the device 510 is collapsible towards the second end portion 518 in response to fluid flow in the second direction 46 similar to the embodiments described above (not shown).

Exemplary techniques for attachment of the flexible member of the flow modifying device in embodiments without a frame include physical adaptations such as barbs or hooks, suturing, stapling, bonding, gluing or otherwise adhering the flow modifying device to the vessel wall 15 or combinations thereof. For example, the device may be secured in place with a tissue adhesive between the flexible member of the device and the vessel wall. Examples of tissue adhesives include, but are not limited to, fibrin glues, TISSEEL®, FLOSEAL®, BIOGLUE®, THOREX®, polyethylene glycol, and bovine or human derived thrombin, fibrinogen, and collagen. The attachment portion may be secured to the vessel wall with bioresorbable sealants and adhesives. Examples of bioresorbable sealants and adhesives include FOCALSEAL® (biodegradable eosin-PEG-lactide hydrogel requiring photopolymerization with Xenon light wand) produced by Focal; BERIPLAST® produced by Adventis-Bering; VIVOSTAT® produced by ConvaTec (Bristol-Meyers-Squibb); SEALAGEN™ produced by Baxter; FIBRX® (containing virally inactivated human fibrinogen and inhibited-human thrombin) produced by CryoLife; TISSEEL® (fibrin glue composed of plasma derivatives from the last stages in the natural coagulation pathway where soluble fibrinogen is converted into a solid fibrin) and TISSUCOL® produced by Baxter; QUIXIL® (Biological Active Component and Thrombin) produced by Omrix Biopharm; a PEG-collagen conjugate produced by Cohesion (Collagen); HYSTOACRYL® BLUE (ENBUCRILATE) (cyanoacrylate) produced by Davis & Geck; NEXACRYL™ (N-butyl cyanoacrylate), NEXABOND™, NEXABOND™ S/C, and TRAUMASEAL™ (product based on cyanoacrylate) produced by Closure Medical (TriPoint Medical); DERMABOND® which consists of 2-octyl cyanoacrylate produced as DERMABOND® by (Ethicon); TISSUEGLU® produced by Medi-West Pharma; and VETBOND® which consists of n-butyl cyanoacrylate produced by 3M.

Alternatively or in addition to adhesives and sealants, anchoring devices may be used for the attachment portion such as barbs and/or hooks known to one skilled in the art. Exemplary attachment methods and devices are described in WO 2004/089253, incorporated by reference in its entirety herein.

The Flow Modifying Device Frame

In some embodiments, the flow modifying device of the present invention may include a frame. Any suitable frame can be used with the flexible member of the present invention. The specific frame chosen will depend on several considerations, including the size and configuration of the vessel at the implantation site and the size and nature of the flow modifying device.

In general, the frame may provide a anchoring function within the vessel. The stent art provides numerous examples of frames acceptable for use with the flow modifying device of the present invention. Exemplary configurations for the frame include, but are not limited to, braided strands, helically wound strands, ring members, consecutively attached ring members, tube members, and frames cut from solid tubes. The specific frame chosen will depend on several factors, including the vessel into which the flow modifying device is being implanted, the axial length of the treatment site, the number of flow modifying devices desired in the device, the inner diameter of the vessel, the delivery method for placing the frame, and others.

The frame may be either balloon- or self-expandable. In some embodiments, the self-expanding frame can be compressed into a low-profile delivery conformation and then constrained within a delivery system for delivery to a point of treatment in the lumen of a body vessel. At the point of treatment, the self-expanding frame can be released and allowed to subsequently expand to another configuration. The frame can be sized so that a second, expanded configuration is slightly larger in diameter that the inner diameter of the vessel in which the medical device will be implanted. This sizing can facilitate anchoring of the flow modifying device within the vessel wall and maintenance of the flow modifying device at a point of treatment following implantation.

Examples of suitable frames for use in the flow modifying device of the present invention include those described in U.S. Pat. Nos. 6,508,833; 6,464,720; 6,231,598; 6,299,635; 4,580,568; and U.S. Publication Nos. 2005/0228472, 2005/0267560, all of which are hereby incorporated by reference in their entirety.

The materials used in the frame can be selected from a well-known list of suitable metals and polymeric materials appropriate for the particular application, depending on necessary characteristics that are required (self-expansion, high radial force, collapsibility, etc.). Suitable metals or metal alloys include: stainless steels (e.g., 316, 316L or 304), nickel-titanium alloys including shape memory or superelastic types (e.g., nitinol or elastinite); inconel; noble metals including copper, silver, gold, platinum, paladium and iridium; refractory metals including molybdenum, tungsten, tantalum, titanium, rhenium, or niobium; stainless steels alloyed with noble and/or refractory metals; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; magnetic ferrite; bioabsorbable materials, including magnesium; or other biocompatible metals and/or alloys thereof.

In various embodiments, the frame comprises a metallic material selected from stainless steel, nickel, silver, platinum, gold, titanium, tantalum, iridium, tungsten, a self-expanding nickel-titanium alloy, a superelastic nickel-titanium alloy sold under the tradename NITINOL or inconel.

One particularly preferred material for forming a frame is a self-expanding material such NITINOL. Other shape memory materials may also be utilized, such as, but not limited to, irradiated memory polymers such as autocrosslinkable high density polyethylene (HDPEX). Shape memory alloys are known in the art and are discussed in, for example, "Shape Memory Alloys," Scientific American, 281: 74-82 (November 1979), incorporated herein by reference.

Some embodiments provide frames that are not self-expanding, or that do not comprise superelastic materials. For example, in other embodiments, the frame can comprise silicon-carbide (SiC). For example U.S. Publication No. 2004/034409, which is incorporated by reference in its entirety herein, discloses various suitable frame materials and configurations.

Other suitable materials that may be used in the frame include, but are not limited to, carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these.

In some embodiments, the frame itself, or any portion of the frame, may include one or more metallic bioabsorbable materials. Suitable metallic bioabsorbable materials include magnesium, titanium, zirconium, niobium, tantalum, zinc and silicon and mixtures and alloys. For example, a zinc-titanium alloy such as discussed in U.S. Pat. No. 6,287,332, which is incorporated herein by reference in its entirety, can be used. The metallic bioabsorbable material can further contain lithium, sodium, potassium, calcium, iron and manganese or mixtures thereof. For example, an alloy containing lithium:magnesium or sodium:magnesium can be used. The physical properties of the frame can be controlled by the selection of the metallic bioabsorbable material, or by forming alloys of two or more metallic bioabsorbable materials. For example, when 0.1% to 1%, percentage by weight, titanium is added to zinc, the brittle quality of crystalline zinc can be reduced. In another embodiment, when 0.1% to 2%, percentage by weight, gold is added to a zinc-titanium alloy, the grain size of the material is reduced upon curing and the tensile strength of the material increases.

The Flexible Member

The flexible member may be formed from a variety of materials known to one of skill in the art. The flexible member may be made from a single material or a combination of materials. The flexible member may be formed from a plurality of layers of materials. The material or materials need only be biocompatible or able to be rendered biocompatible. The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

In some embodiments, the flexible member may be formed from material from a human or non-human primate origin. After harvesting, such Xenogenic or cadaveric material may be cryopreserved or chemically fixed, such as by cross-linking. Such treatment methods are known to those practicing the art and include, but are not limited to, chemical fixation using aldehydes, such as formaldehyde or glutaraldehyde. Prior to chemical fixing, these materials may be treated to remove cellular components. Examples of such decellularization treatments are disclosed in U.S. Pat. No. 5,595,571, the contents of which are incorporated by this reference. In addition, various other treatment techniques may be used to mitigate problems caused by the calcification of chemically-fixed material. Examples of such techniques are disclosed in U.S. Pat. Nos. 4,553,974 and 6,547,827, the contents of which are incorporated by reference.

In some embodiments, the flow modifying device of the present invention, or portions thereof, including the flexible member, may comprise a bioabsorbable material that can be degraded and absorbed by the body over time to advantageously eliminate the portion formed from the bioabsorbable material from the vessel before, during or after the remodeling process. A number of bioabsorbable homopolymers, copolymers, or blends of bioabsorbable polymers are known in the medical arts. These include, but are not necessarily limited to, polyesters including poly-alpha hydroxy and poly-beta hydroxy polyesters, polycaprolactone, polyglycolic acid, polyether-esters, poly(p-dioxanone), polyoxaesters; polyphosphazenes; polyanhydrides; polycarbonates including polytrimethylene carbonate and poly(iminocarbonate); polyesteramides; polyurethanes; polyisocyantes; polyphosphazines; polyethers including polyglycols polyorthoesters; expoxy polymers including polyethylene oxide; polysaccharides including cellulose, chitin, dextran, starch, hydroxyethyl starch, polygluconate, hyaluronic acid; polyamides including polyamino acids, polyester-amides, polyglutamic acid, poly-lysine, gelatin, fibrin, fibrinogen, casein, and collagen.

Examples of biocompatible homo- or co-polymers suitable for use in the present invention include vinyl polymers including polyfumarate, polyvinylpyrolidone, polyvinyl alcohol, poly-N-(2-hydroxypropyl)-methacrylamide, polyacrylates, and polyalkylene oxalates.

Reconstituted or naturally-derived collagenous materials can be used in the present invention. Such materials that are at least bioresorbable will provide advantage in the present invention, with materials that are bioremodelable and promote cellular invasion and ingrowth providing particular advantage.

Suitable bioremodelable materials can be provided by collagenous extracellular matrix materials (ECMs) possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material. See, C. Heeschen et al., *Nature Medicine* 7 (2001), No. 7, 833-839. When combined with a fluorescence microangiography technique, this model can provide both quantitative and qualitative measures of angiogenesis into biomaterials. C. Johnson et al., *Circulation Research* 94 (2004), No. 2, 262-268.

In certain embodiments of the invention, the flexible member material is a biocompatible polyurethane. One example of a biocompatible polyurethane is THORALON (THORATEC, Pleasanton, Calif.), as described in U.S. Pat. Nos. 4,675,361 and 6,939,377, both of which are incorporated herein by reference. According to these patents, THORALON is a polyurethane base polymer (referred to as BPS-215) blended with a siloxane containing surface modifying additive (referred to as SMA-300). Base polymers containing urea linkages can also be used. The concentration of the surface modifying additive may be in the range of 0.5% to 5% by weight of the base polymer.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON can be manipulated to provide either porous or non-porous THORALON. Porous THORALON can be formed by mixing the polyetherurethane urea (BPS-215), the surface modifying additive (SMA-300) and a particulate substance in a solvent. The particulate may be any of a variety of different particulates or pore forming agents, including inorganic salts. Preferably the particulate is insoluble in the solvent. The solvent may include dimethyl formamide (DMF), tetrahydrofuran (THF), dimethyacetamide (DMAC), dimethyl sulfoxide (DMSO), or mixtures thereof. The composition can contain from about 5 wt % to about 40 wt % polymer, and different levels of polymer within the range can be used to fine tune the viscosity needed for a given process. The composition can contain less than 5 wt % polymer for some spray application embodiments. The particulates can be mixed into the composition. For example, the mixing can be performed with a spinning blade mixer for about an hour under ambient pressure and in a temperature range of about 18° C. to about 27° C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water for the extraction, for example water at a temperature of about 60° C. The resulting pore diameter can also be substantially equal to the diameter of the salt grains.

The porous polymeric sheet can have a void-to-volume ratio from about 0.40 to about 0.90. Preferably the void-to-volume ratio is from about 0.65 to about 0.80. The resulting void-to-volume ratio can be substantially equal to the ratio of salt volume to the volume of the polymer plus the salt. Void-to-volume ratio is defined as the volume of the pores divided by the total volume of the polymeric layer including the volume of the pores. The void-to-volume ratio can be measured using the protocol described in AAMI (Association for the Advancement of Medical Instrumentation) VP20-1994, Cardiovascular Implants-Vascular Prosthesis section 8.2.1.2, Method for Gravimetric Determination of Porosity. The pores in the polymer can have an average pore diameter from about 1 micron to about 400 microns. Preferably the average pore diameter is from about 1 micron to about 100 microns, and more preferably is from about 1 micron to about 10 microns. The average pore diameter is measured based on images from a scanning electron microscope (SEM). Formation of porous THORALON is described, for example, in U.S. Pat. No. 6,752,826 and US Publication No. 2003/0149471, both of which are incorporated herein by reference.

Non-porous THORALON can be formed by mixing the polyetherurethane urea (BPS-215) and the surface modifying additive (SMA-300) in a solvent, such as dimethyl formamide (DMF), tetrahydrofuran (THF), dimethyacetamide (DMAC), dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments. The entire composition can be cast as a sheet, or coated onto an article such as a mandrel or a mold. In one example, the composition can be dried to remove the solvent.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

A variety of other biocompatible polyurethanes/polycarbamates and urea linkages (hereinafter "—C(O)N or CON type polymers") may also be employed. These include CON type polymers that preferably include a soft segment and a hard segment. The segments can be combined as copolymers or as blends. For example, CON type polymers with soft segments such as PTMO, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

Preferably, the hard segment is formed from a diisocyanate and diamine. The diisocyanate may be represented by the formula OCN—R—NCO, where —R— may be aliphatic, aromatic, cycloaliphatic or a mixture of aliphatic and aromatic moieties. Examples of diisocyanates include MDI, tetramethylene diisocyanate, hexamethylene diisocyanate, trimethyhexamethylene diisocyanate, tetramethylxylylene diisocyanate, 4,4'-dicyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3'-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

Other applicable biocompatible polyurethanes include those using a polyol as a component of the hard segment. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, 1,6-hexanediol, 1,8-octanediol, propylene glycols, 2,3-butylene glycol, dipropylene glycol, dibutylene glycol, glycerol, or mixtures thereof.

Biocompatible CON type polymers modified with cationic, anionic and aliphatic side chains may also be used. See, for example, U.S. Pat. No. 5,017,664.

Other biocompatible CON type polymers include: segmented polyurethanes, such as BIOSPAN; polycarbonate urethanes, such as BIONATE; and polyetherurethanes, such as ELASTHANE; (all available from POLYMER TECHNOLOGY GROUP, Berkeley, Calif.).

Other biocompatible CON type polymers can include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ally, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Publication No. 2002/0187288, which is incorporated herein by reference.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

In another embodiment of the invention, the flexible member material is formed from or coated with a polyparaxylene ("parylene") or a parylene derivative, for example parylene C or parylene N. For example, the parylene or parylene derivative is created by first heating p-xylene or a suitable derivative at an appropriate temperature (for example, at about 950° C.) to produce the cyclic dimer di-p-xylylene (or a derivative thereof). The resultant solid can be separated in pure form, and then cracked and pyrolyzed at an appropriate temperature (for example, at about 680° C.) to produce a monomer vapor of p-xylylene (or derivative); the monomer vapor is cooled to a suitable temperature (for example, below 50° C.) and the flexible member is formed by vapor phase deposition.

Attachment of the Flexible Member to the Frame

The flexible member material can be attached to the frame by any appropriate attachment means, including but not limited to, sewing, adhering, heat sealing, tissue welding, weaving, sonically bonding. Cross-linking or otherwise joining the flexible member to the frame. Alternatively, the flexible member may be formed on the support structure by an appropriate means, including but not limited to vapor deposition, spraying, electrostatic deposition, ultrasonic deposition, or dipping.

In one embodiment, the flexible member may be formed from ECM and sewn to the frame. Alternatively, the flexible member formed from ECM may be formed as a sheet, folded over the frame and adhered to itself using adhesive or sonic bonding and the like.

In one embodiment of the invention, the flow modifying device prosthesis includes a flexible member formed from a non-porous biocompatible polyurethane based polymer such as non-porous THORALON. According to one method of attachment, a solution comprising a dissolved THORALON is coated and dried on a mandril to form a flexible member.

A solution for forming non-porous THORALON can be made by mixing the polyetherurethane urea (BPS-215) and the surface modifying additive (SMA-300) in a solvent, such as dimethyl formamide (DMF), tetrahydrofuran (THF), dimethyacetamide (DMAC), or dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments.

The entire composition can be cast as a sheet, or coated onto an article such as a mandril or a mold. In one example, the composition can be dried to remove the solvent. The mandril can be made from any suitable material that permits the THORALON to coated, dried on and removed from the mandril surface. Suitable materials include stainless steel and glass. In one embodiment, at least a portion of the outer surface of the mandril is formed in the desired shape of a flexible member. The flexible member can be formed by coating a thin layer of a solution of THORALON onto the shaped portion of the mandril, drying the coating of the THORALON on the mandril surface, and carefully removing the dried layer of THORALON. The dried layer in the desired shape for the flexible member may be delivered and adhered to the vessel wall without a frame or the dried layer may be attached to the frame.

The flexible member can be attached to the frame by any suitable technique. In one embodiment, the flexible member comprises THORALON that is attached to the frame by being formed around and encapsulating portions of the frame. In one method, a solution comprising dissolved THORALON is sprayed and dried on an assembly formed by fitting at least a portion of the frame over a mandril to form a flow modifying device prosthesis comprising the flexible member.

In one embodiment, one or more pre-coating layer(s) of THORALON are coated onto at least a portion of the mandril. Next, the frame is fitted onto the mandril. The frame can be any of those described above. Third, a solution comprising a DMAC solution of non-porous THORALON is coated onto the assembly comprising the mandril and the frame using any suitable method, including spraying or dipping.

In one embodiment, a solution of THORALON is sprayed from a spray gun onto the assembly and the mandril is rotated during spraying process to promote uniform coating of the mandril. Any suitable rate of rotation can be used that provides for a uniform coating of the mandril and retains the coated material on the surface of the mandril. In one embodiment, the mandril is rotated at a rate of about 1 rpm.

When a pre-coating layer is present on the mandril, the THORALON adheres to the pre-coating layer as the solution of THORALON is spray coated onto the surface of the assembly and forms a sheet of THORALON that encapsulates portions of the frame. Optionally, one or more bioactive agents (described below) can be coated onto the mandril with the THORALON.

In one embodiment, the pre-coating layer is first dried on the mandril, then the support frame is placed over the coated mandril, and finally second layer of THORALON is spray coated over the support frame as a solution comprising a suitable solvent such as DMAC and THORALON. The solvent in the spray solution preferably partially solubilizes the pre-coating layer so that one fused layer of THORALON is formed. The fused layer can encapsulate portions of the frame and be solidified by evaporation of residual solvent, thereby joining the THORALON to the frame. The residual solvent in the fused layer can be evaporated by heating the flow modifying device prosthesis on the mandril.

Alternatively, the flexible member can be attached to the support frame by other methods. In one embodiment, a sheet of material is cut to form a flexible member and an edge of the flexible member may be wrapped around portions of a frame and portions of the flexible member sealably connected together to fasten the flexible member around the support frame. For example, one edge of the flexible member can be wrapped around a portion of the frame and held against the body of the flexible member, so that the flexible member material forms a lumen enclosing a portion of the frame. A small amount of a suitable solvent is then applied to the edge of the flexible member material to dissolve the edge into an adjacent portion of the flexible member material and thereby seal the material around the frame.

In another embodiment, the sheet of material is shaped to form the flexible member that is attached to a portion of a frame using stitching through the flexible member material and around a portion of the support structure, adhesives, tissue welding or cross linking to directly join the flexible member material to the frame. A flexible member attached to a frame can be permitted to move relative to the frame, or portions of the flexible member can be substantially fixed in position or orientation with respect to the frame by using attachment configurations that resist relative movement of the portion of the flexible member and the frame.

An electrostatic spray deposition (ESD) method of coating the flexible member material onto a mandril can also be used to form a flexible member. In this embodiment, particles in the sprayed solution of flexible member material are electrostatically charged when leaving the nozzle of the spray gun and the mandril is maintained at an electrical potential or grounded to attract the charged particles from the sprayed solution of flexible member material. The solution of material is first dissolved in a solvent and then sprayed onto the mandril using an ESD process.

The ESD process generally depends on the principle that a charged particle is attracted towards a grounded target. Without being confined to any theory, the typical ESD process may be described as follows. The solution that is to be deposited on the mandril is typically charged to several thousand volts (typically negative) and the mandril held at ground potential. The charge of the solution is generally great enough to cause the solution to jump across an air gap of several inches before landing on the target. As the solution is in transit towards the target, it fans out in a conical pattern which aids in a more uniform coating. In addition to the conical spray shape, the charged particles are further attracted towards the conducting portions of the target, rather than towards any non-conductive region of the target, leaving the coating mainly on the conducting regions of the target.

Generally, the ESD method allows for control of the coating composition and surface morphology of the deposited coating. In particular, the morphology of the deposited coating may be controlled by appropriate selection of the ESD parameters, as set forth in WO 03/006180 (Electrostatic Spray Deposition (ESD) of biocompatible coatings on Metallic Substrates), the contents of which are incorporated herein by reference. For example, a coating having a uniform thickness and grain size, as well as a smooth surface, may be obtained by controlling deposition conditions such as deposition temperature, spraying rate, precursor solution, and bias voltage between the spray nozzle and the medical device being coated. The deposition of porous coatings is also possible with the ESD method.

One hypothetical example of an electrostatic spraying apparatus and method is provided. Specifically, a solution of a non-porous THORALON material could be loaded into a 20 mL syringe of an ESD apparatus from Terronics Development Corp. (Elwood, Ind.), which can then be mounted onto a syringe pump and connected to a tub that carries the solution to a spray head. The syringe pump could then used to purge the air from the solution line and prime the line and spray nozzle with solution. An electrical connection to the nozzle could supply the required voltage. An electrical connection could be provided to hold the mandril at grounding potential.

A motor could then be activated to rotate the mandril at a constant speed of about 1 rpm. The syringe pump could then be activated to supply the nozzle with a consistent flow of solution, and the power supply could be activated to provide a charge to the solution and cause the solution to jump the air gap and land on the mandril surface. As the coated surface is rotated away from the spray path, the volatile portion of the solution could be evaporated leaving a coating of THORALON behind. The mandril could be continually rotated in the spray pattern until the desired amount of non-porous THORALON material accumulates. During the coating process, the mandril could preferably be kept at ambient temperature and humidity, the solution could be pumped at a rate of about 2-4 $cm^3$/hr through the spray gun (which can be placed at a horizontal distance of approximately 6 cm from the mandril), and the bias voltage between the spray nozzle and the mandril should be approximately 10-17 kilovolts.

A frame could then be slipped over a mandril (Terronics Development Corp., 2 mm×30 mm) so that at least a portion of the support frame makes an electrical connection with the mandril. The mandril could again be continually rotated in the spray pattern until the desired amount of non-porous THORALON material accumulates.

Where it is desired that portions of the perimeter of the flexible member material are not attached to the frame, the flexible member material may be cut to free the material from the frame. Alternatively, a mask may be used to cover portions of the frame to prevent attachment of THORALON. The mask can be made from any suitable material that permits the THORALON to coated, dried on and removed from the mask surface. In one embodiment, a mask could be applied to the mandril surface before application of pre-coating layer(s) of THORALON. After the pre-coating layer(s) are applied, the mask could be removed and the frame placed on the mandril. The mandril could again be continually rotated in the spray pattern until the desired amount of non-porous THORALON material accumulates. Only those portions of the frame placed over portions of the mandril having a pre-coating of THORALON would be enclosed in THORALON.

Further examples of methods of preparation of flow modifying device prostheses, including methods of attaching a flexible member to a frame, can be found in U. S. Publication No. US 2007-0027535.

Bioactive Agents

The flow modifying device of the present invention can include a bioactive agent. A bioactive agent can be included in any suitable part of the flow modifying device, for example in the frame and/or the flexible member. Selection of the type of bioactive agent, the portions of the flow modifying device comprising the bioactive agent, and the manner of attaching the bioactive agent to the flow modifying device can be chosen to perform a desired therapeutic function upon implantation and, in particular, to achieve controlled release of the bioactive agent.

For example, a therapeutic bioactive agent can be combined with a biocompatible polyurethane, impregnated in an extracellular collagen matrix material, incorporated in the support structure or coated over any portion of the flow modifying device. In one embodiment, the flow modifying device can comprise a flexible member comprising a bioactive agent coated on the surface of the flexible member or impregnated in the flexible member. In another aspect, a bioactive material is combined with a biodegradable polymer to form a portion of the frame.

A bioactive agent can be incorporated in or applied to portions of the flow modifying device by any suitable method that permits controlled release of the bioactive agent material and the effectiveness thereof for an intended purpose upon implantation in the body vessel. The configuration of the bioactive agent on or in the flow modifying device will depend in part on the desired rate of elution for the bioactive agent. Bioactive agents can be coated directly on the flow modifying device surface or can be adhered to a flow modifying device surface by means of a coating. For example, a bioactive agent can be blended with a polymer and spray or dip coated on the flow modifying device surface. For example, a bioactive agent material can be posited on the surface of the flow modifying device and a porous coating layer can be posited over the bioactive agent material. The bioactive agent material can diffuse through the porous coating layer. Multiple porous coating layers and or pore size can be used to control the rate of diffusion of the bioactive agent material. The coating layer can also be nonporous wherein the rate of diffusion of the bioactive agent material through the coating layer is controlled by the rate of dissolution of the bioactive agent material in the coating layer.

The bioactive agent material can also be dispersed throughout the coating layer, by for example, blending the bioactive agent with the polymer solution that forms the coating layer.

If the coating layer is biostable, the bioactive agent can diffuse through the coating layer. If the coating layer is biodegradable, the bioactive agent is released upon erosion of the biodegradable coating layer.

Bioactive agents may be bonded to the coating layer directly via a covalent bond or via a linker molecule which covalently links the bioactive agent and the coating layer. Alternatively, the bioactive agent may be bound to the coating layer by ionic interactions including cationic polymer coatings with anionic functionality on bioactive agent, or alternatively anionic polymer coatings with cationic functionality on the bioactive agent. Hydrophobic interactions may also be used to bind the bioactive agent to a hydrophobic portion of the coating layer. The bioactive agent may be modified to include a hydrophobic moiety such as a carbon based moiety, silicon-carbon based moiety or other such hydrophobic moiety. Alternatively, the hydrogen bonding interactions may be used to bind the bioactive agent to the coating layer.

The bioactive agent can optionally be applied to or incorporated in any suitable portion of the flow modifying device. The bioactive agent can be applied to or incorporated in the flow modifying device, a polymer coating applied to the flow modifying device, a material attached to the flow modifying device or a material forming at least a portion of the flow modifying device. The bioactive agent can be incorporated within the material forming the frame, or within pores formed in the surface of the frame. The flow modifying device can optionally comprise a coating layer containing the bioactive agent, or combinations of multiple coating layers configured to promote a desirable rate of elution of the bioactive from the flow modifying device upon implantation within the body.

A coating layer comprising a bioactive agent can comprise a bioactive agent and a biostable polymer, a biodegradable polymer or any combination thereof. In one embodiment, the bioactive agent is blended with a biostable polymer to deposit the bioactive agent within the porous channels within the biostable polymer that permit elution of the bioactive agent from the flow modifying device prosthesis upon implantation. Alternatively, a blend of the bioactive and the bioabsorbable polymer can be incorporated within a biostable polymer matrix to permit dissolution of the bioabsorbable polymer through channels or pores in the biostable polymer matrix upon implantation in the body, accompanied by elution of the bioactive agent.

Multiple coating layers can be configured to provide a flow modifying device with a desirable bioactive agent elution rate upon implantation. The flow modifying device can comprise a diffusion layer positioned between a portion of the flow modifying device that comprises a bioactive agent and the portion of the flow modifying device contacting the body upon implantation. For example, the diffusion layer can be a porous layer positioned on top of a coating layer that comprises a bioactive agent. The diffusion layer can also be a porous layer positioned on top of a bioactive agent coated on or incorporated within a portion of the flow modifying device.

A porous diffusion layer is preferably configured to permit diffusion of the bioactive agent from the flow modifying device upon implantation within the body at a desirable elution rate. Prior to implantation in the body, the diffusion layer can be substantially free of the bioactive agent. Alternatively, the diffusion layer can comprise a bioactive agent within pores in the diffusion layer. Optionally, the diffusion layer can comprise a mixture of a biodegradable polymer and a bioactive positioned within pores of a biostable polymer of a diffusion layer. In another embodiment, the porous diffusion layer can comprise a mixture of a biodegradable polymer and a biostable polymer, configured to permit absorption of the biodegradable polymer upon implantation of the flow modifying device prosthesis to form one or more channels in the biostable polymer to permit an underlying bioactive agent to diffuse through the pores formed in the biostable polymer.

In one aspect of the invention, the bioactive agent is an antithrombogenic bioactive agent. Flow modifying devices comprising an antithrombogenic bioactive agent are particularly preferred for implantation in areas of the body that contact blood. An antithrombogenic bioactive agent is any therapeutic agent that inhibits or prevents thrombus formation within a body vessel. The flow modifying device can comprise any suitable antithrombogenic bioactive agent. Types of antithrombotic bioactive agents include anticoagulants, antiplatelets, and fibrinolytics. Anticoagulants are bioactive agents which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid is dissolution of a thrombus. Examples of antithrombotics include but are not limited to anticoagulants such as thrombin, Factor Xa, Factor VIIa and tissue factor inhibitors; antiplatelets such as glycoprotein IIIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51, 7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Other examples of bioactive coating compounds include antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as (GP) $II_b/III_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methyl-prednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus (rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin; pimecrolimus; angiopeptin; HMG co-enzyme reductase inhibitors (statins); metalloproteinase inhibitors (batimastat); protease inhibitors; antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat. Still other bioactive agents that can be incorporated in or coated on a frame include a PPAR α-agonist, a PPAR δ agonist and RXR agonists, as disclosed in published U.S. Publication No. 2004/0073297 incorporated in its entirety herein by reference.

Delivery of the Flow Modifying Device

The flow modifying device of the present invention may be delivered to a lumen of a body vessel by various techniques known in the art. By way of non-limiting example, the flow modifying device may be delivered and positioned in the body vessel using a catheter. For delivery, the flow modifying device may be placed in a folded or unexpanded configuration to fit in the lumen of a delivery catheter. The catheter is then introduced into the body vessel and its tip positioned at a point of treatment within the body vessel. The flow modifying device may then be expelled from the tip of the catheter at the point of treatment. Once expelled from the catheter, the flow modifying device may expand to the expanded configuration and engage the interior wall of the body vessel, preferably using an attachment portion or the frame provided on the flow modifying device. The flow modifying device may be self-expanding or expandable by a balloon of a balloon catheter as will be understood by one of skill in the art. Delivery has been described using a delivery catheter as an example, the flow modifying device may be delivered to a position within a body by any means known to one of skill in the art. Exemplary delivery devices suitable for implanting the flow modifying device include U.S. Publication Nos. 2004/0225344 and 2003/0144670, which are incorporated by reference herein in their entirety.

EXAMPLE 1

An embodiment of the prosthetic flow modifying device was tested to determine the flow rate through the flow modifying device and the reflux percentage through the flow modifying device at different pressures (mmHg). Briefly, the flow modifying device was placed in a flow testing device having a constant level reservoir. The height of the reservoir was adjusted to create the desired pressure head for measuring the flow through the flow modifying device. The pressure heads used in Example 1 were 2, 10, 50 and 80 mm Hg. Water was used in the reservoir at 37° C.

The results of the flow testing are shown in the Table 1 below. The mean flow rate represents an average of 3 measurements for each condition presented in the table. Table 1 shows the results using a flow modifying device similar to the flow modifying device shown in FIGS. 7A and 7B having a frame with struts extending inward and a flexible member.

TABLE 1

| Pressure Head (mmHg) | Orientation | n | Mean Flow Rate ml/min | Reflux Percentage R/A * 100 |
|---|---|---|---|---|
| 2 | Antegrade | 3 | 1248.723 | |
| 2 | Retrograde | 3 | 1165.181 | 93.30981716 |
| 10 | Antegrade | 3 | 1562.782 | |
| 10 | Retrograde | 3 | 1463.977 | 93.67759482 |
| 50 | Antegrade | 3 | 2656.662 | |
| 50 | Retrograde | 3 | 1467.162 | 55.01457214 |
| 80 | Antegrade | 3 | 3301.409 | |
| 80 | Retrograde | 3 | 1456.1 | 44.10541948 |

As shown in Table 1, the mean flow rate through the flow modifying device in the second, retrograde direction is reduced in comparison to the mean flow through the flow modifying device in the first, antegrade direction. As the pressure increases, for example at 50 and 80 mm Hg, the reflux percentage decreases due to greater collapsing of collapsible member.

Although the invention herein has been described in connection with a preferred embodiment thereof, it will be appreciated by those skilled in the art that additions, modifications, substitutions, and deletions not specifically described may be made without departing from the spirit and scope of the invention as defined in the appended claims. The scope of the invention is defined by the appended claims, and all devices that come within the meaning of the claims, either literally or by equivalence, are intended to be embraced therein.

The invention claimed is:

1. An implantable prosthetic device for modifying fluid flow through a body lumen, the device comprising:

a flexible member configured for permitting fluid flow through the body in a first direction at a first rate and for restricting fluid flow through the body lumen in a second direction at a second rate, the flexible member comprising;

a passageway defined by a sheath of biocompatible material, the passageway with a first end portion and a second end portion;

the first end portion sized and shaped to at least partially restrict fluid flow in the first direction and capable of at least partially collapsing in response to fluid flow in the second direction; and the second end portion adapted to seal with a wall of the body lumen;

wherein a diameter of a first opening defined in the first end portion is smaller than a diameter of a second opening defined in the second end portion;

wherein the device comprises a frame operably connected to the flexible member; and wherein the frame comprises at least one strut operably connected to the first end portion and configured for extending inward into the body lumen.

2. The prosthetic device of claim 1 wherein the frame comprises a material selected from the group consisting of stainless steel, nickel, silver, platinum, gold, titanium, tantalum, iridium, tungsten, a self-expanding nickel titanium alloy and inconel.

3. The prosthetic device of claim 1, wherein the flexible member is adherable to the lumen wall for implantation.

4. The prosthetic device of claim 1, wherein the device comprises at least one biocompatible synthetic material.

5. The prosthetic device of claim 1, wherein the device comprises a bioremodelable material.

6. The prosthetic device of claim 1, wherein the flexible member comprises cryopreserved or cross-linked xenogenic tissue.

7. An implantable prosthetic device for modifying fluid flow through a body lumen, the device comprising:
    a flexible member configured for permitting fluid flow through the body in a first direction at a first rate and for restricting fluid flow through the body lumen in a second direction at a second rate, the flexible member comprising;
    a passageway defined by a sheath of biocompatible material, the passageway with a first end portion and a second end portion;
    the first end portion sized and shaped to at least partially restrict fluid flow in the first direction and capable of at least partially collapsing in response to fluid flow in the second direction; and
    the second end portion adapted to seal with a wall of the body lumen;
    wherein a diameter of a first opening defined in the first end portion is smaller than a diameter of a second opening defined in the second end portion;
    wherein the first end portion further comprises an edge portion extending at least partially into the lumen to at least partially restrict fluid flow in the first direction.

8. The prosthetic device of claim 1, wherein the first end portion is configured to invert towards the second end portion when fluid flow is in the second direction.

9. The prosthetic device of claim 1, wherein the flexible member comprises a plurality of layers of biocompatible materials.

10. A prosthetic device for implantation in a body vessel, the prosthetic device comprising:
    a flexible member moveable between an open configuration and a closed configuration, the flexible member comprising:
    a passageway defined by a sheath of biocompatible material, the passageway having a first end portion and a second end portion operably connected to the first end portion; and
    a frame operably connected to the second end portion;
    wherein the first end portion at least partially restricts fluid flow through the passageway in the open configuration and wherein the first end portion is at least partially collapsible toward the second end portion to form the closed configuration when fluid flow is in a second direction;
    wherein the frame comprises at least one strut operably connected to the first end portion and extending inward toward a central portion of the lumen.

11. The prosthetic device of claim 10, wherein the first end portion is conically shaped.

12. The prosthetic device of claim 10, wherein at least the second end portion is tubular shaped.

13. The prosthetic device of claim 10, wherein the first end portion comprises an edge portion surrounding the first opening and extending generally perpendicularly to the body vessel when the device is implanted.

14. A prosthetic device for implantation in a body vessel, the prosthetic device comprising:
    a flexible member moveable between an open configuration and a closed configuration, the flexible member comprising:
    a passageway defined by a sheath of biocompatible material, the passageway having a first end portion and a second end portion operably connected to the first end portion; and
    a frame operably connected to the second end portion;
    wherein the first end portion at least partially restricts fluid flow through the passageway in the open configuration and wherein the first end portion is at least partially collapsible toward the second end portion to form the closed configuration when fluid flow is in a second direction;
    wherein the first end portion comprises an edge portion surrounding the first opening and extending generally perpendicularly to the body vessel when the device is implanted; and
    wherein the edge portion further comprises at least one opening defined through the edge portion.

* * * * *